(12) United States Patent
Turchetta et al.

(10) Patent No.: US 8,518,988 B2
(45) Date of Patent: Aug. 27, 2013

(54) POLYMORPH OF THE HYDROCHLORIDE OF THE (4-HYDROXYCARBAMOYL-PHENYL)-CARBAMIC ACID (6-DIMETHYLAMINO METHYL-2-NAPHTHALENYL) ESTER

(75) Inventors: Stefano Turchetta, Patricia (IT); Maurizio Zenoni, Patraicia (IT)

(73) Assignee: Chemi SPA, Cinisello Balsamo (IT)

( * ) Notice: Subject to any disclaimer, the term of this patent is extended or adjusted under 35 U.S.C. 154(b) by 0 days.

(21) Appl. No.: 13/575,641

(22) PCT Filed: Dec. 3, 2010

(86) PCT No.: PCT/IB2010/055560
§ 371 (c)(1),
(2), (4) Date: Jul. 27, 2012

(87) PCT Pub. No.: WO2011/092556
PCT Pub. Date: Aug. 4, 2011

(65) Prior Publication Data
US 2012/0302633 A1    Nov. 29, 2012

(30) Foreign Application Priority Data

Jan. 28, 2010  (IT) .............................. MI2010A0121

(51) Int. Cl.
*A01N 37/00*    (2006.01)
*A61K 31/21*    (2006.01)
*A61K 9/20*     (2006.01)

(52) U.S. Cl.
USPC .......................................... 514/506; 424/464

(58) Field of Classification Search
None
See application file for complete search history.

(56) References Cited

U.S. PATENT DOCUMENTS 6,034,096 A    3/2000  Bertolini et al.
7,329,689 B2 *  2/2008  Pinori et al. .................. 514/485

OTHER PUBLICATIONS

Byrn, Stephen et al. "Pharmaceutical Solids: A Strategic Approach to Regulatory Considerations," Pharmaceutical Research, vol. 12, No. 7, pp. 945-954, Jul. 1, 1995, XP000996386.

* cited by examiner

*Primary Examiner* — Fereydoun G Sajjadi
*Assistant Examiner* — Michael B Pallay
(74) *Attorney, Agent, or Firm* — Lucas & Mercanti, LLP

(57) ABSTRACT

Herein described is a novel crystalline form of the hydrochloride of the (4-hydroxycarbamoyl-phenyl)-carbamic acid (6-dimethylamino methyl-2-naphtalenyl) ester. In particular, herein described is a polymorph of the hydrochloride of the (4-hydroxycarbamoyl-phenyl)-carbamic acid (6-dimethylamino methyl-2-naphtalenyl) ester, characterized by a Powder X Ray Diffraction spectrum as indicated in FIG. 1, and/or by a DSC profile as indicated in FIG. 2, and/or by a TGA profile as indicated in FIG. 3 and/or by an IR spectrum as indicated in FIG. 4.

14 Claims, 5 Drawing Sheets

PXRD profile of form II of ITF 2357

DSC profile of form II of ITF 2357

TGA profile of form II of ITF 2357

FTIR profile of form II of ITF 2357

Profile of the stability diffractograms of form II of ITF 2357 at 40°C, 75% relative humidity

- ○ T = 0 (first profile from the bottom)
- ○ T = 2 days (second profile from the bottom),
- ○ T = 7 days (third profile from the bottom)
- ○ T = 15 days (fourth profile from the bottom)

POLYMORPH OF THE HYDROCHLORIDE OF THE (4-HYDROXYCARBAMOYL-PHENYL)-CARBAMIC ACID (6-DIMETHYLAMINO METHYL-2-NAPHTHALENYL) ESTER

This application is a U.S. National Stage of PCT/IB2010/055560 filed Dec. 3, 2010, which claims priority to and the benefit of Italian Application No. MI2010A000121 filed Jan. 28, 2010, the contents of which applications are incorporated herein by reference in their entirety.

The hydrochloride of the (4-hydroxycarbamoyl-phenyl)-carbamic acid (6-dimethylamino methyl-2-naphtalenyl) ester, also known as ITF 2357 and having the International Non Proprietary Name (INN) of Givinostat® is an organic compound with immunosuppressive and anti-inflammatory activity, currently undergoing clinical tests for several diseases related to the deacetylase histone inhibitor capacity thereof.

The structure of such molecule is reported below.

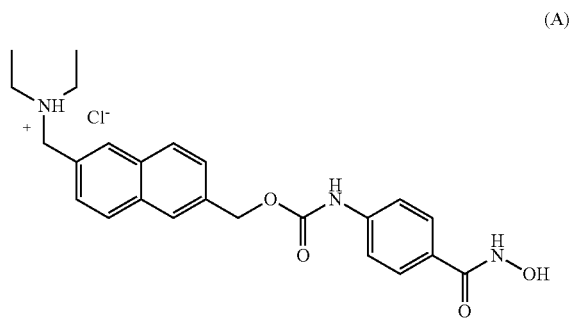

(A)

BACKGROUND OF THE INVENTION

U.S. Pat. No. 6,034,096 reports the preparation of (A) while U.S. Pat. No. 7,329,689 indicates the characteristics and the preparation of a monohydrate polymorph form of the compound (A), called polymorph form I.

U.S. Pat. No. 6,034,096, example 12, actually reports the preparation of compound (A) wherein the product is isolated as a white solid having a melting point of 162-165° C. (with decomposition). In U.S. Pat. No. 7,329,689, with reference to U.S. Pat. No. 6,034,096, it is stated that the product obtained according to U.S. Pat. No. 6,034,096 is an anhydrous, amorphous, hygroscopic and deliquescent product, difficult to handle. A novel monohydrate crystalline form of the compound (A), particularly advantageous for industrial use in that it is stable and easier to handle with respect to the anhydrous product described previously, is actually described in U.S. Pat. No. 7,329,689.

BRIEF DESCRIPTION OF THE INVENTION

A subject of the present invention is a novel polymorph form of the compound (A), and methods for the preparation thereof. The novel crystalline form subject of the present invention shall be indicated from now henceforth as polymorph form II of the compound (A) and it is characterized by the property of having a greater water solubility with respect to the monohydrate described in U.S. Pat. No. 7,329,689, i.e. the polymorph form I of the compound (A).

DETAILED DESCRIPTION OF THE INVENTION

During the experiments aimed at identifying novel solid forms of the compound (A), the novel crystalline form II of such compound, whose water solubility characteristics are more favourable with respect to the known monohydrate form I, in that the novel form II has greater solubility with respect to form I was surprisingly discovered. Such characteristic of the novel polymorph is particularly interesting given that the water solubility of a compound has an impact on the bioavailability of such compound (see Pharmaceutical Research, Vol. 12, n. 3, 1995, page 413 "*correlations between in vitro dissolution and in vivo bioavailability are extensive. . . .*"), hence outlining the possibility of administering the compound (A) in a more bioavailable form, increasing the possibilities of using the active ingredient and contributing to diversifying dosages thereof.

As a matter of fact, a comparative experiment between form I of the compound (A) (monohydrate prepared as described in U.S. Pat. No. 7,329,689) and form II of compound (A), subject of the present invention, was carried out.

10 mg of compound (A) in crystalline form I were agitated in 10 ml of a 0.9% sodium chloride solution (isotonic solution) at 37° C. for 24 hours. The concentration of the product in liquid phase was measured at the end.

Table 1 indicates the obtained solubility data.

TABLE 1

|  | Solubility (mg/ml) | Relative solubility vs. form I |
|---|---|---|
| Form I | 0.154 | 1.00 |
| Form II | 0.226 | 1.47 |

The indicated data show that the novel form II is 1.47 times more soluble than the known form I.

Figure 1:
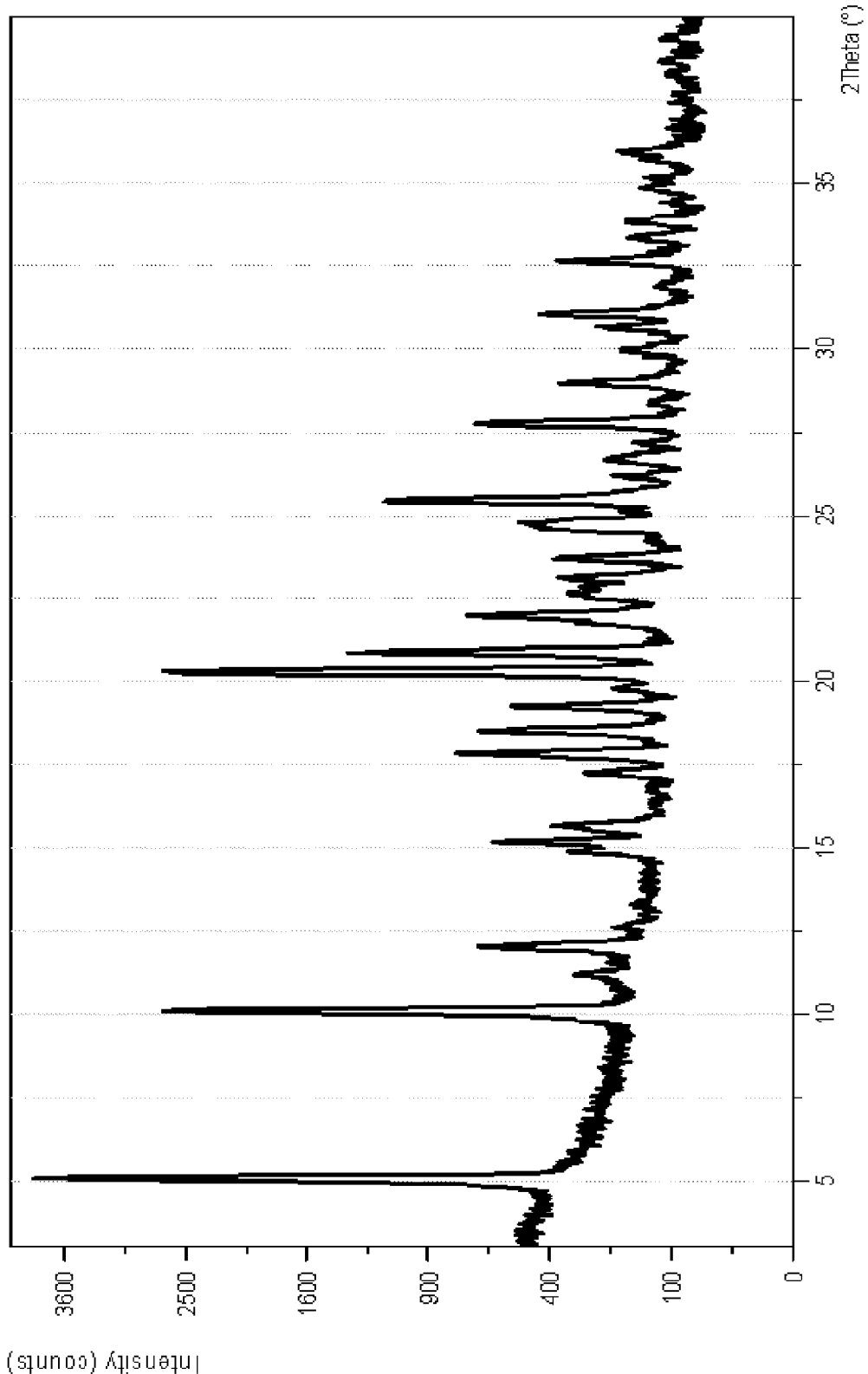
FIG. 1 describes the PXRD profile of form II of ITF 2357.
Figure 2:
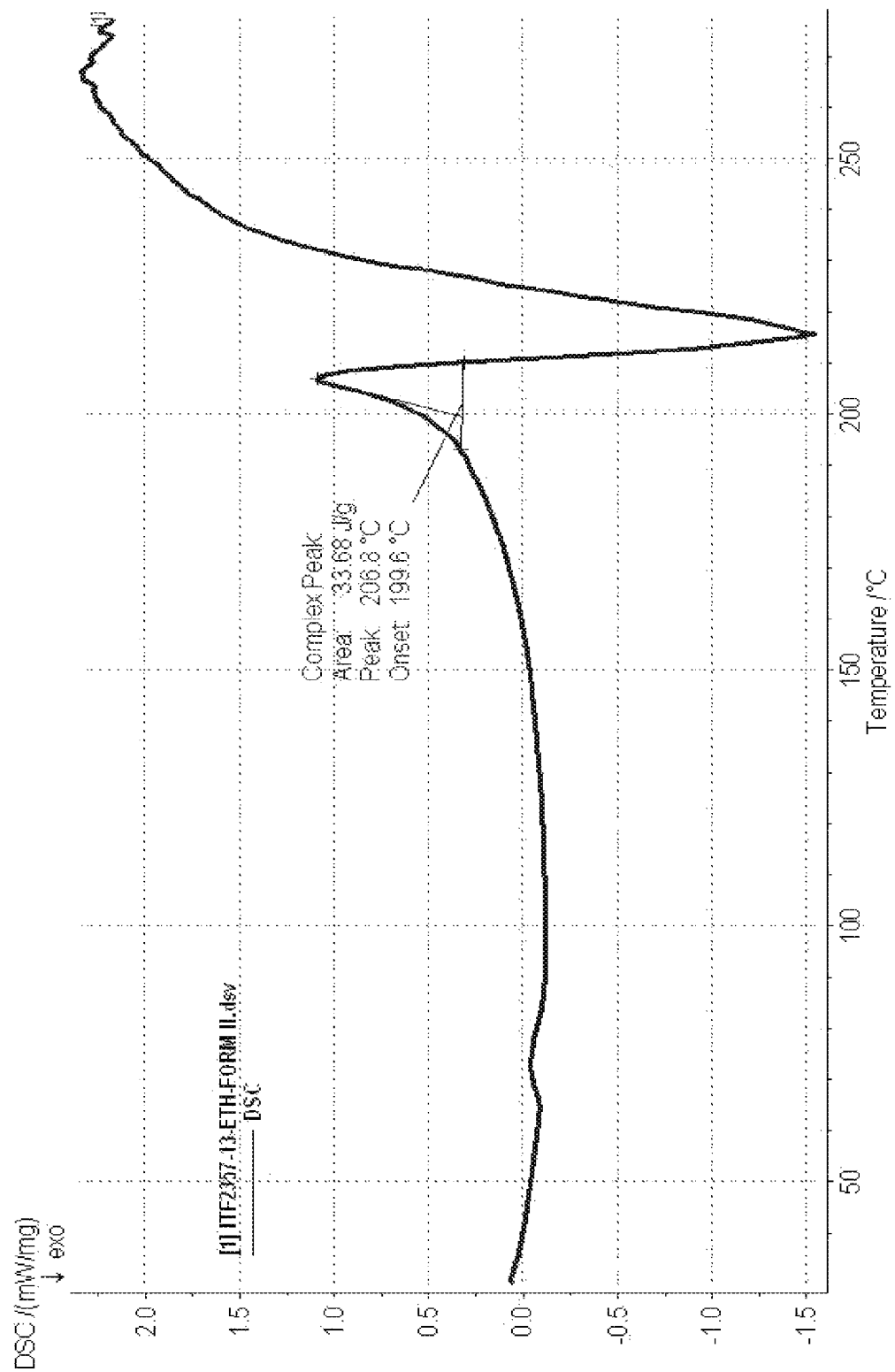
FIG. 2 describes the DSC profile of form II of ITF 2357.
Figure 3:
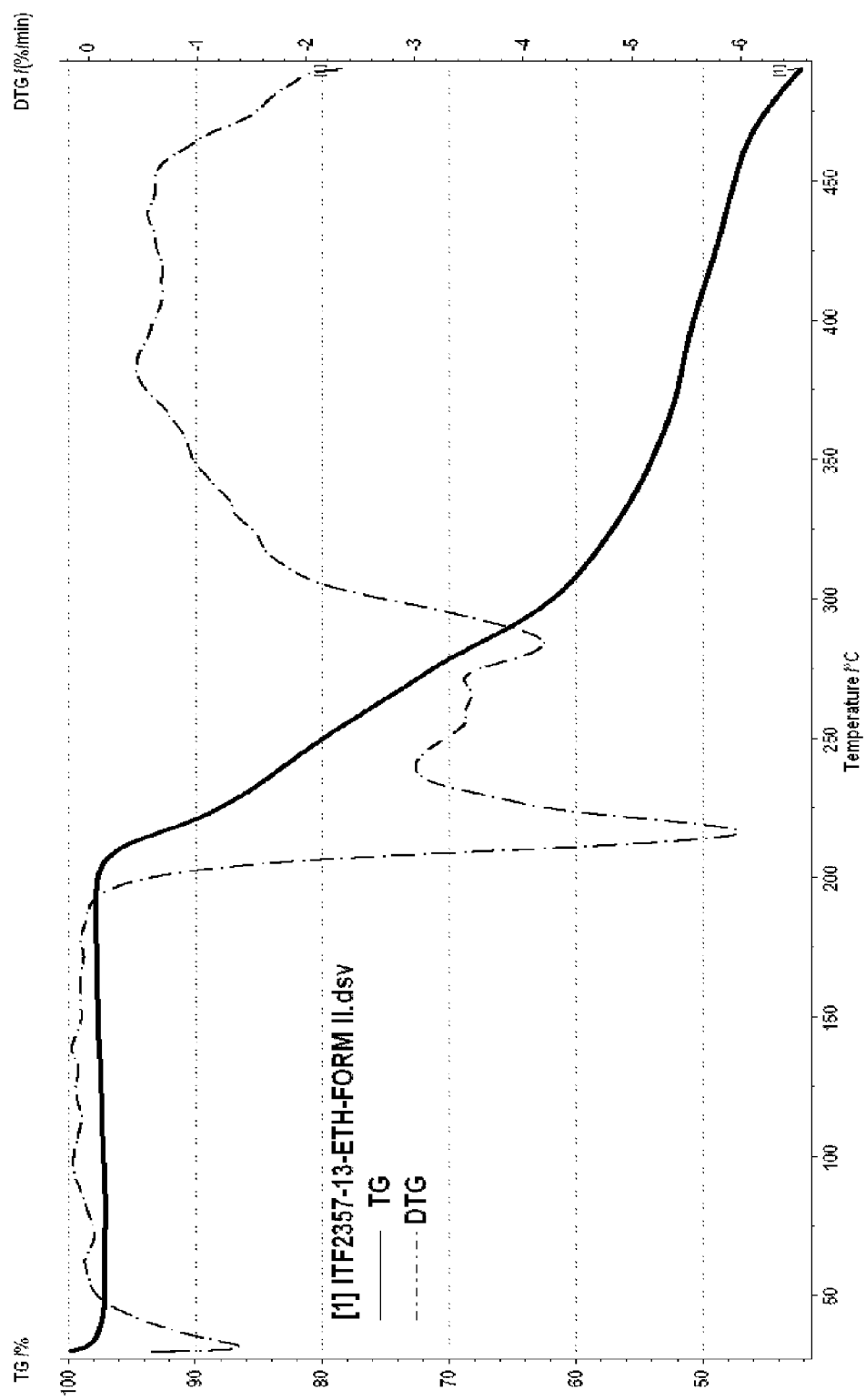
FIG. 3 describes the TGA profile of form II of ITF 2357.
Figure 4:
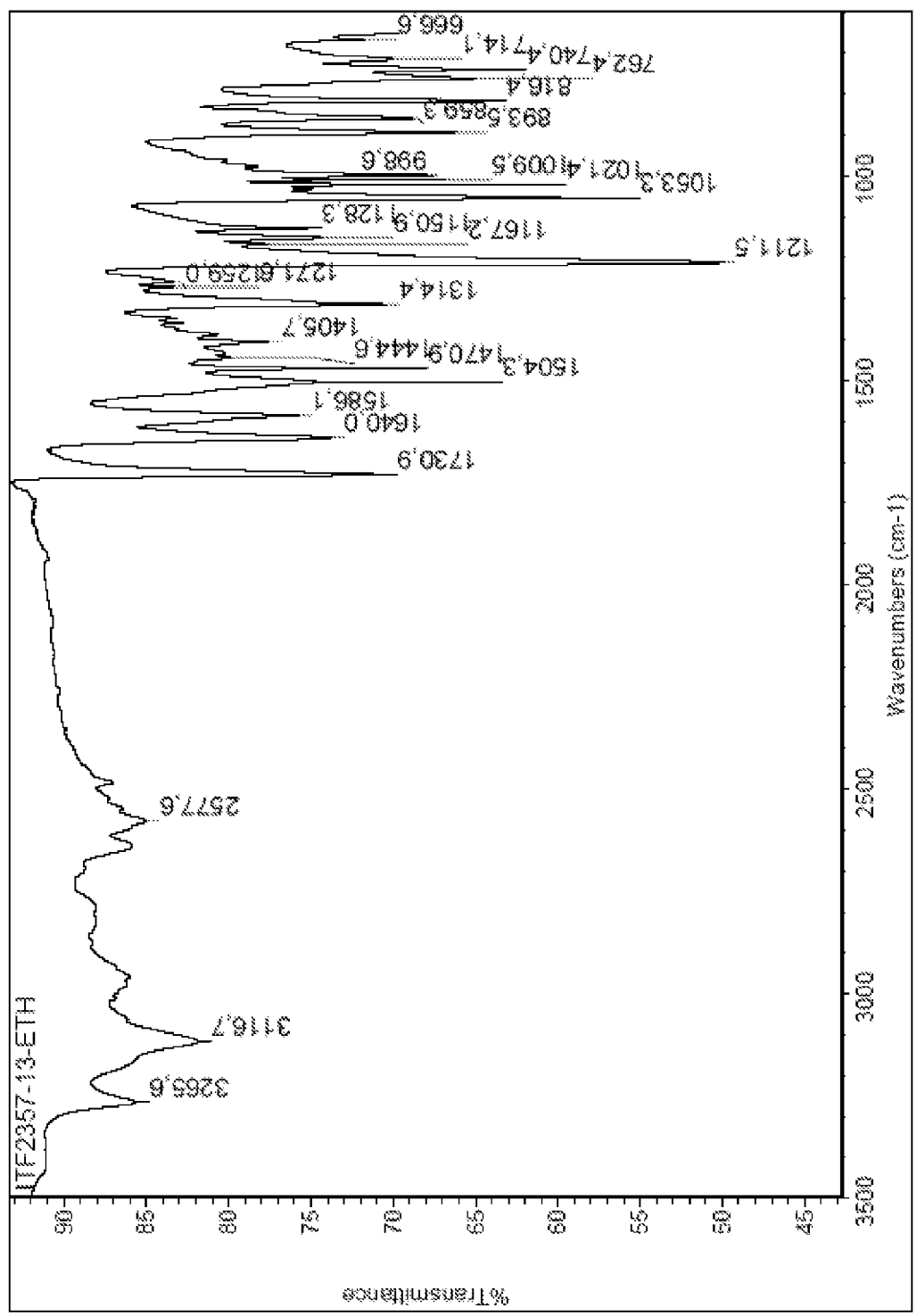
FIG. 4 describes the FTIR profile of form II of ITF 2357.

The crystalline form II of ITF 2357 is characterised by a powder X-ray diffractogram profile (PXRD) as exemplified in FIG. 1 and/or by a DSC profile as exemplified in FIG. 2 and/or by a TGA profile (thermogravimetry) as exemplified in FIG. 3 and/or by an FTIR (Fourier transform infrared spectroscopy) profile was exemplified in FIG. 4.

The characteristic peaks that distinguish the aforementioned PXRD, DSC, TGA and FTIR charts, are those indicated below.

Thus, a subject of the present invention is the hydrochloride of the (4-hydroxycarbamoyl-phenyl)-carbamic acid (6-dimethylamino methyl-2-naphtalenyl) ester in the crystalline form II, characterised by the Powder X-ray diffractogram profile (PXRD) indicated in FIG. 1, whose characteristic peaks are observed at the following positions 2 theta: 5.10; 10.07; 14.90; 15.15; 15.67; 17.24; 17.84; 18.51; 19.23; 20.25; 20.37; 22.01; 22.63; 23.12; 24.76; 25.40; 27.78; 28.97; 31.02 degrees, with a margin of error on the value indicated for each peak of ±0.20 degrees (2 theta).

Table 2 indicates the data regarding peaks observed in the PXRD diffractogram.

The crystalline form II is characterised by the DSC profile indicated in FIG. 2. Such chart shows an endothermic peak—due to the melting of the product—with Peak onset at 199.6° C., Peak at 206.8° C. and melting enthalpy of 33.7 Joules/g. A preferred embodiment of the invention is therefore represented by crystalline form II of ITF 2357 having a DSC profile showing an endothermic peak with Peak onset between 199 and 201° C., Peak between 206 and 207° C. and melting enthalpy between 15 and 40 Joules/g.

The crystalline form II of the hydrochloride of the (4-hydroxycarbamoyl-phenyl)-carbamic acid (6-dimethylamino methyl-2-naphtalenyl) ester is characterized by the TGA profile indicated in FIG. 3. Such chart does not show significant change in mass loss until beyond 200° C., where a progressive mass loss probably due to the degradation of the sample starts. The crystalline form II of the hydrochloride of the (4-hydroxycarbamoyl-phenyl)-carbamic acid (6-dimethylamino methyl-2-naphtalenyl) ester is characterised by the FTIR spectrum indicated in FIG. 4 (dispersion in Nujol) whose characteristic peaks are observed at the following frequencies: 3265; 3117; 2578; 1731; 1640; 1556; 1 504; 1471; 1406; 1314; 1272; 1259; 1212; 1167; 1151; 1128; 1055; 1021; 1010; 999; 894; 859; 816; 762; 740; 714 $cm^{-1}$, with a margin of error on the indicated value for each peak of ±2 ($cm^{-1}$).

TABLE 2

| Pos. [*2Th.] | Height [cts] | FWHM [*2Th.] | d-spacing [Å] | Rel. Int. [%] |
|---|---|---|---|---|
| 3.5057 | 18.22 | 0.6691 | 25.20339 | 0.53 |
| 5.0947 | 3419.85 | 0.1338 | 17.34591 | 100.00 |
| 10.0732 | 2259.55 | 0.1673 | 8.78139 | 66.07 |
| 11.1841 | 136.14 | 0.1004 | 7.91151 | 3.98 |
| 12.0262 | 483.84 | 0.1506 | 7.35939 | 14.15 |
| 12.6534 | 39.73 | 0.2007 | 6.99598 | 1.16 |
| 14.9038 | 207.59 | 0.0836 | 5.94427 | 6.07 |
| 15.1546 | 443.60 | 0.1338 | 5.84646 | 12.97 |
| 15.6734 | 213.97 | 0.1171 | 5.65409 | 6.26 |
| 17.2397 | 150.43 | 0.1004 | 5.14375 | 4.40 |
| 17.8380 | 629.52 | 0.1171 | 4.97257 | 18.41 |
| 18.5102 | 523.98 | 0.1506 | 4.79347 | 15.32 |
| 19.2346 | 374.91 | 0.1171 | 4.61456 | 10.96 |
| 19.8049 | 82.19 | 0.1338 | 4.48294 | 2.40 |
| 20.2478 | 2352.43 | 0.0836 | 4.38587 | 68.79 |
| 20.3694 | 1804.49 | 0.0836 | 4.35996 | 52.77 |
| 20.8622 | 1175.35 | 0.1506 | 4.25807 | 34.37 |
| 21.7398 | 133.23 | 0.1004 | 4.08813 | 3.90 |
| 22.0071 | 583.96 | 0.1673 | 4.03907 | 17.08 |
| 22.6302 | 212.76 | 0.0836 | 3.92925 | 6.22 |
| 22.8803 | 160.67 | 0.1171 | 3.88686 | 4.70 |
| 23.1245 | 223.35 | 0.1338 | 3.84636 | 6.53 |
| 23.6751 | 233.54 | 0.1171 | 3.75815 | 6.83 |
| 24.5784 | 268.10 | 0.1338 | 3.62204 | 7.84 |
| 24.7640 | 350.77 | 0.0836 | 3.59531 | 10.26 |
| 25.4012 | 989.41 | 0.0836 | 3.50655 | 28.93 |
| 26.1634 | 83.67 | 0.1673 | 3.40610 | 2.45 |
| 26.6452 | 109.44 | 0.2676 | 3.34560 | 3.20 |
| 27.2107 | 36.57 | 0.1171 | 3.27734 | 1.07 |
| 27.7833 | 564.94 | 0.1673 | 3.21108 | 16.52 |
| 28.4008 | 28.72 | 0.1338 | 3.14265 | 0.84 |
| 28.9678 | 251.19 | 0.0836 | 3.08242 | 7.34 |
| 29.9611 | 74.49 | 0.2007 | 2.98245 | 2.18 |
| 30.6880 | 168.54 | 0.0502 | 2.91344 | 4.93 |
| 31.0225 | 314.48 | 0.1506 | 2.88279 | 9.20 |
| 31.8474 | 42.24 | 0.1338 | 2.80998 | 1.24 |
| 32.6256 | 290.56 | 0.1171 | 2.74471 | 8.50 |
| 33.3718 | 97.84 | 0.1171 | 2.68502 | 2.86 |
| 33.8378 | 94.40 | 0.2007 | 2.64910 | 2.76 |

TABLE 2-continued

| Pos. [*2Th.] | Height [cts] | FWHM [*2Th.] | d-spacing [Å] | Rel. Int. [%] |
|---|---|---|---|---|
| 34.8422 | 72.58 | 0.1004 | 2.57501 | 2.12 |
| 35.7113 | 56.21 | 0.1171 | 2.51430 | 1.64 |
| 35.9699 | 112.50 | 0.1004 | 2.49682 | 3.29 |
| 38.6888 | 23.63 | 0.1673 | 2.32739 | 0.69 |
| 39.3127 | 40.39 | 0.2007 | 2.29188 | 1.18 |

The crystalline form II of ITF 2357 subject of the present invention may be obtained through various crystallisation techniques. For example, it may be obtained through crystallisation of the amorphous product as obtained in example 12 of U.S. Pat. No. 6,034,096, from solvents such as alcohols, esters, ketones, ethers, amides, aromatic hydrocarbons, aliphatic hydrocarbons, nitriles and/or mixtures thereof. In particular $C_1$-$C_6$ alcohol solvents, $C_1$-$C_6$ alkyl esters of $C_1$-$C_6$ carboxylic acids are preferred. Even more in particular, the form II is obtained through crystallisation of ITF 2357 from methanol, ethanol, n-propanol, isopropanol, n-butanol, 2-methoxyethanol, isobutanol and mixtures of methanol with esters such as methyl formate, ethyl acetate, isopropyl acetate, n-propyl acetate, diethyl carbonate and ethyl benzoate, from mixtures of methanol with ethers such as 1,4-dioxane, THF, 1,2-dimethoxyethane, diisopropyl ether and t-butyl-methyl ether, from mixtures of acetone with amides such as dimethylformamide and dimethylacetamide, from a mixture of methanol and benzonitrile, from a mixture of benzyl alcohol with methylcyclohexane, from a mixture of methanol and toluene.

Figure 5:
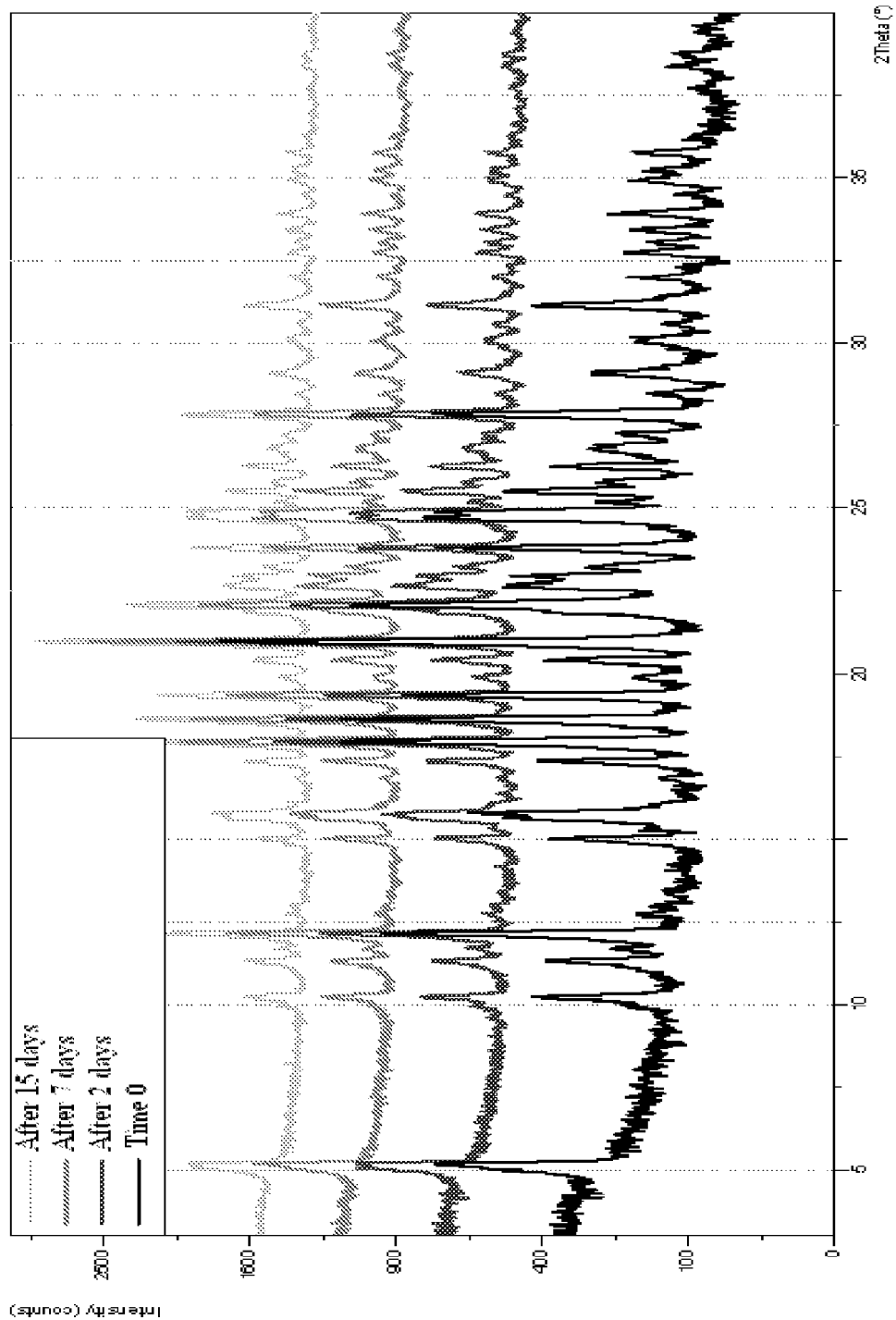
FIG. 5 describes the profile of the stability diffractograms of ITF 2357 of form II at 40° C., 75% relative humidity at different times. In particular, the first diffractogram from the bottom is performed at time 0, the second diffractogram from the bottom is performed after 2 days, the third diffractogram from the bottom is performed after 7 days and the fourth diffractogram from the bottom is performed after 15 days.

Stability tests were performed on form II of ITF 2357, revealing that such crystalline form is stable. In detail, a sample of form II of ITF 2357 was deposited in a thin layer having a thickness of about 0.5 cm on a Petri dish and placed in an environment with a constant humidity of 75%, at a constant temperature of 40° C. for two weeks. Samples were taken after 2, 7 and 15 days and analysed through Powder X Ray Diffraction (PXRD). The results of such experiments were summarised in FIG. 5, where the diffractograms obtained from the samples of the various collections were indicated overlapped. FIG. 5 clearly shows that no modifications of the crystalline form was observed in any of the examined samples and thus that the crystalline form II of ITF 2357 shows high stability even under stressed storage conditions.

Also the pharmaceutical formulations comprising the hydrochloride of the (4-hydroxycarbamoyl-phenyl)-carbamic acid (6-dimethylamino methyl-2-naphtalenyl) ester in crystalline form II and a pharmaceutically acceptable excipient and/or adjuvant, form a subject of the present invention where such formulations are preferably solid and even more preferably in form of tablets.

The following examples clarify in detail the conditions used for obtaining form II of ITF 2357, but they shall not be deemed restrictive as regards with the scope of protection of the present invention.

Experimental Part

Characterisation of ITF 2357 crystalline form II was carried out through the following spectroscopic techniques, according to the following experimental conditions:

Experimental Conditions

| PXRD (Power X Ray Diffraction) | |
|---|---|
| Type of instrument: | X'Pert PRO PANalytical |
| Type of measurement | One scan |
| Measurement wavelength | Cu Kα1 |
| Material constituting the anode: | Cu |
| X-Ray tube voltage: | 40 |
| X-Ray tube current (mA): | 40 |
| Type of movement of the sample: | Rotation |
| Time of rotation of the sample (s): | 1.0 |
| Thickness of the filter (mm): | 0.020 |
| Material of the filter: | Ni |
| Name of the detector: | X'Celerator |
| Type of detector: | RTMS detector |
| Scan axis: | Gonio |
| Scan range (°): | 3.0000-39.9987 |
| Amplitude of the range of measurement (°): | 0.0167 |
| N° of points: | 2214 |
| Scan mode: | Continuous |
| Time of count (s): | 12.700 |
| Application software: | X'Pert Data Collector vs. 2.2d |
| Instrument control software: | XPERT-PRO vs. 1.9B |
| Temperature | Ambient temperature |
| FTIR | |
| Type of instrument: | Nicolet FT-IR 6700 ThermoFischer |
| Spectral range (Standard): | 7800-350 $cm^{-1}$ |
| Spectral range (Option, CsI Optics): | 6400-200 $cm^{-1}$ |
| Spectral range (Option, Extended-Range Optics): | 11000-375 $cm^{-1}$ |
| Spectral range (Option, Multi-Range Optics): | 27000-15 $cm^{-1}$ |
| Optical resolution: | 0.09 $cm^{-1}$ |
| Peak to peak background noise (1 minute scan): | <8.68 × $10^{-6}$ AU* |
| RMS background noise (1 minute scan): | <1.95 × $10^{-6}$ AU* |
| Ordinate linearity: | 0.07% T |
| Wavelength accuracy: | 0.01 cm-1 |
| Minimum linear scan speed: | 0.158 cm/sec |
| Maximum linear scan speed: | 6.33 cm/sec |
| Scan speed number: | 15 |
| Quick scan (Spectra/second @ 16 cm−1, 32 cm−1): | 65.95 |
| Number of sample scans: | 32 |
| Number of background scans: | 32 |
| Resolution: | 4.000 $cm^{-1}$ |
| Sample gain: | 8.0 |
| Optical speed: | 0.6329 |
| Opening: | 100.00 |
| Detector: | DTGS KBr |
| Ray baffle: | KBr |
| Source: | IR |
| DSC/TGA | |
| Type of instrument: | STA 409 PC Luxx ® Netzsch |
| Heating and cooling speed: | 0.01 K/min ... 50 K/min |
| TG resolution: | up to 0.00002% |
| DSC resolution: | <1 μW (K sensor) |
| DSC sensitivity | 8 μV/mW (K sensor) |
| Atmosphere: | Inert (Nitrogen) |
| Control of the gas flow: | 2 flush gas and 1 protection gas |
| Flush gas: | Nitrogen |
| Flush gas speed: | 60 ml/min |
| Protection gas: | Nitrogen |
| Protection gas speed: | 20 ml/min |
| Crucible: | DSC/TG pan Al |
| Heating speed: | 10° C./min |
| DSC heating ramp: | 30° C. to 280° C. |
| TGA heating ramp: | 40° C. to 500° C. |

EXAMPLES

The preparation of ITF 2357 used as starting material in the following examples, may be performed through the methods described in U.S. Pat. No. 6,034,096 or in U.S. Pat. No. 7,329,689.

Example 1

Preparation of ITF2357 in Crystalline Form II by Crystallisation from Methanol 4.0 g of ITF 2357 are introduced into a 250 ml flask, followed by 80 ml of methanol. The mixture is agitated and heated to reflux until complete dissolution of the solid. The reflux is maintained for 15', then the mixture is cooled until 25° C., leaving under agitation under such conditions for one hour. Then, the obtained solid is filtered on buchner, washing with 10 ml of methanol. This allows obtaining 3.1 g of moist solid which is dried in a rotary evaporator at 45° C. for one night under vacuum (45 mmHg). 2.1 g of ITF 2357 are obtained in crystalline form II, as confirmed by the PXRD analysis.

Example 2

Preparation of ITF2357 in Crystalline Form II by Resuspension in Ethanol 4.0 g of ITF 2357 and 180 ml of absolute ethanol are added into a 250 ml flask. The mixture is brought to reflux under agitation, the insoluble still present is filtered at such temperature, washed with ethanol and dried at 45° C. under vacuum (45 mmHg) for 10 hours, obtaining 2.8 g of ITF 2357 in crystalline form II.

Example 3

Preparation of ITF2357 in Crystalline Form II by Resuspension in Isopropanol 4.0 g of ITF 2357 and 40 ml of isopropanol are added into a 250 ml flask. The mixture is kept under agitation at 25° C. for 8 hours, then the resulting solid is filtered and it is washed using 10 ml of isopropanol. The obtained product is dried for 16 hours at 40° C. under vacuum (50 mmHg), obtaining 3.7 g of ITF 2357 in crystalline form II.

Example 4

Preparation of ITF2357 in Crystalline Form II by Crystallisation from Methanol-Acetone 5.0 g of ITF 2357 and 70 ml of methanol are added into a 250 ml flask and brought to reflux temperature (65° C.); complete solution is observed at such temperature. 44 ml of acetone are thus added to the solution in about 20 minutes. Precipitation of some crystals is observed. The temperature is brought to 25° C., with formation of an abundant precipitate. It is thus cooled to 5° C. and it is left under agitation under such conditions for 30 minutes. Then, the solid is filtered on buchner, washing it with 10 ml of acetone. 5.4 g of a moist solid, which is dried under vacuum (50 mmHg) at 45° C. for 12 hours are obtained. 4.2 g of ITF 2357 in crystalline form II are thus obtained.

Example 5

Preparation of ITF2357 in Crystalline Form II by Crystallisation from Methanol-methyl-t-butyl ether 5.0 g of ITF 2357 and 70 ml of methanol are added into a 250 ml flask and brought to the reflux temperature (65° C.); complete solution is observed at such temperature. 14 ml of methyl-t-butyl ether are thus added to the solution in about 10 minutes.

The temperature is brought to 25° C., with formation of an abundant precipitate and it is left under agitation under such conditions for 30 minutes. Then, the solid is filtered on buchner, washing it with 10 ml of methyl-t-butyl ether. 4.9 g of a moist solid, which is dried under vacuum (50 mmHg) at 45° C. for 12 hours, are obtained. 4.5 g of ITF 2357 in crystalline form II are thus obtained.

The invention claimed is:

1. Hydrochloride of the (4-hydroxycarbamoyl-phenyl)-carbamic acid (6-dimethylamino methyl-2-naphtalenyl) ester in crystalline form II, characterised in that it has a Powder X Ray Diffraction spectrum having the following peaks ±0.20° (2 theta): 5.10; 10.07; 14.90; 15.15; 15.67; 17.24; 17.84; 18.51; 19.23; 20.25; 20.37; 22.01; 22.63; 23.12; 24.76; 25.40; 27.78; 28.97; 31.02.

2. Hydrochloride of the (4-hydroxycarbamoyl-phenyl)-carbamic acid (6-dimethylamino methyl-2-naphtalenyl) ester in crystalline form II, according to claim 1, having a DSC profile showing an endothermic peak with Peak onset at 199-201° C., Peak at 206-207° C. and melting enthalpy of 15-40 Joule/g.

3. Hydrochloride of the (4-hydroxycarbamoyl-phenyl)-carbamic acid (6-dimethylamino methyl-2-naphtalenyl) ester in crystalline form II, according to claim 1, having a DSC profile showing an endothermic peak with Peak onset at 199.6° C., Peak at 206.8° C. and melting enthalpy of 33.7 Joule/g.

4. Hydrochloride of the (4-hydroxycarbamoyl-phenyl)-carbamic acid (6-dimethylamino methyl-2-naphtalenyl) ester in crystalline form II, according to claim 1, characterised by a TGA profile wherein no significant change in mass loss is observed until about 200° C.

5. Hydrochloride of the (4-hydroxycarbamoyl-phenyl)-carbamic acid (6-dimethylamino methyl-2-naphtalenyl) ester in crystalline form II according to claim 1, having an FTIR spectrum showing the following peaks (±2 $cm^{-1}$): 3265; 3117; 2578; 1731; 1640; 1556; 1 504; 1471; 1406; 1314; 1272; 1259; 1212; 1167; 1151; 1128; 1055; 1021; 010; 999; 894; 859; 816; 762; 740; 714 $cm^{-1}$.

6. Solid pharmaceutical formulations comprising the hydrochloride of the (4-hydroxycarbamoyl-phenyl)-carbamic acid (6-dimethylamino methyl-2-naphtalenyl) ester in crystalline form II according to claim 1 and at least one pharmaceutically acceptable excipient and/or adjuvant.

7. Pharmaceutical formulations according to claim 6, in form of tablets.

8. Method for obtaining the hydrochloride of the (4-hydroxycarbamoyl-phenyl)-carbamic acid (6-dimethylamino methyl-2-naphtalenyl) ester in crystalline form II, according to claim 1, comprising subjecting the hydrochloride of the (4-hydroxycarbamoyl-phenyl)-carbamic acid (6-dimethylamino methyl-2-naphtalenyl) ester to crystallisation from solvents selected from the group consisting essentially of alcohols, esters, ketones, ethers, amides, aromatic hydrocarbons, aliphatic hydrocarbons, nitriles and mixtures thereof.

9. Method according to claim 8, wherein the solvents are $C_1$-$C_6$ alcohols and/or $C_1$-$C_6$ alkyl esters of $C_1$-$C_6$ carboxylic acids.

10. Method according to claim 9, wherein the solvent is methanol, ethanol, n-propanol, isopropanol, n-butanol, 2-methoxyethanol, or isobutanol.

11. Method according to claim 8, wherein the solvent is a mixture of methanol with esters, a mixture of methanol with ethers, a mixture of acetone with amides, a mixture of methanol and benzonitrile, a mixture of benzyl alcohol and methylcyclohexane, or a mixture of methanol and toluene.

12. Method according to claim 11, wherein the mixture of methanol with esters comprises methyl formate, ethyl acetate, isopropyl acetate, n-propyl acetate, diethyl carbonate, or ethyl benzoate.

13. Method according to claim 11, wherein the mixture of methanol with ethers comprises 1,4-dioxane, THF, 1,2-dimethoxyethane, diisopropyl ether, or t-butyl-methyl ether.

14. Method according to claim 11, wherein the mixture of acetone with amides comprises dimethylformamide or dimethylacetamide.

* * * * *

UNITED STATES PATENT AND TRADEMARK OFFICE
CERTIFICATE OF CORRECTION

PATENT NO. : 8,518,988 B2
APPLICATION NO. : 13/575641
DATED : August 27, 2013
INVENTOR(S) : S. Turchetta et al.

It is certified that error appears in the above-identified patent and that said Letters Patent is hereby corrected as shown below:

On the Title Page

Column 1, item (75) Inventors,

Stefano Turchetta, Patricia (IT) should read "Stefano Turchetta, Patrica (IT)"

Maurizio Zenoni, Patraicia (IT) should read "Maurizio Zenoni, Patrica (IT)"

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,518,988 B2
APPLICATION NO. : 13/575641
DATED : August 27, 2013
INVENTOR(S) : Turchetta et al.

It is certified that error appears in the above-identified patent and that said Letters Patent is hereby corrected as shown below:

On the Title Page

The Abstract, lines 2-3:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

The Abstract, lines 4-5:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

In the Specification

Col. 1, lines 1-5:
(4-HYDROXYCARBAMOYL-PHENYL)-CARBAMIC ACID (6-DImEHTYLAMINO METHYL-2-NAPHTHALENYL) ESTER should read "4-HYDROXYCARBAMOYL-PHENYL)-CARBAMIC ACID (6-DIEHTYLAMINO METHYL-2-NAPHTHALENYL) ESTER"

Col. 1, lines 12-14:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 2, lines 61-62:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 3, lines 14-15:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Signed and Sealed this
Third Day of February, 2015

Michelle K. Lee
*Deputy Director of the United States Patent and Trademark Office*

CERTIFICATE OF CORRECTION (continued)
U.S. Pat. No. 8,518,988 B2

Col. 3, lines 21-22:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 4, lines 50-51:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

In the Claims

Col. 7, lines 19-20, Claim 1:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 7, lines 26-27, Claim 2:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 7, lines 32-33, Claim 3:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 7, lines 38-39, Claim 4:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 7, lines 43-44, Claim 5:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 8, lines 7-8, Claim 6:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 8, lines 13-15, Claim 8:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"

Col. 8, lines 17-18, Claim 8:
(4-hydroxycarbamoyl-phenyl)-carbamic acid (6-dimethylamino methyl-2-naphthalenyl) ester should read "(4-hydroxycarbamoyl-phenyl)-carbamic acid (6-diethylamino methyl-2-naphthalenyl) ester"